United States Patent [19]

Jones

[11] Patent Number: 4,781,898
[45] Date of Patent: Nov. 1, 1988

[54] AUTOCLAVE VENT

[75] Inventor: Arthur L. Jones, Charlotte, N.C.

[73] Assignee: Pelton and Crane Company, Charlotte, N.C.

[21] Appl. No.: 45,969

[22] Filed: May 1, 1987

[51] Int. Cl.$^4$ .............................................. A61L 2/06
[52] U.S. Cl. .................................... 422/295; 422/26; 422/105; 422/108; 422/112; 422/305
[58] Field of Search .................... 422/116, 26, 27, 105, 422/112, 108, 292, 295, 305

[56] References Cited

U.S. PATENT DOCUMENTS 4,309,381  1/1982  Chamberlain et al. .................. 422/3
4,447,399  5/1984  Runnells et al. ..................... 422/116

FOREIGN PATENT DOCUMENTS 3409381 10/1986 Fed. Rep. of Germany.

Primary Examiner—Barry S. Richman
Assistant Examiner—Jill Johnston
Attorney, Agent, or Firm—Lawrence C. Edelman

[57] ABSTRACT

The sterilizing pressure chamber of an autoclave is provided with two valve controlled vent paths. At the end of the sterilizing cycle of the autoclave a first vent path channels the sterilizing steam from the chamber into a condensing coil having an end which opens into a liquid reservoir. When the pressure within the chamber drops to a predetermined level, a second vent path, having a flow rate which is greater than the first path, opens and provides a channel for the rapid escape of the remainder of the steam from the chamber.

9 Claims, 1 Drawing Sheet

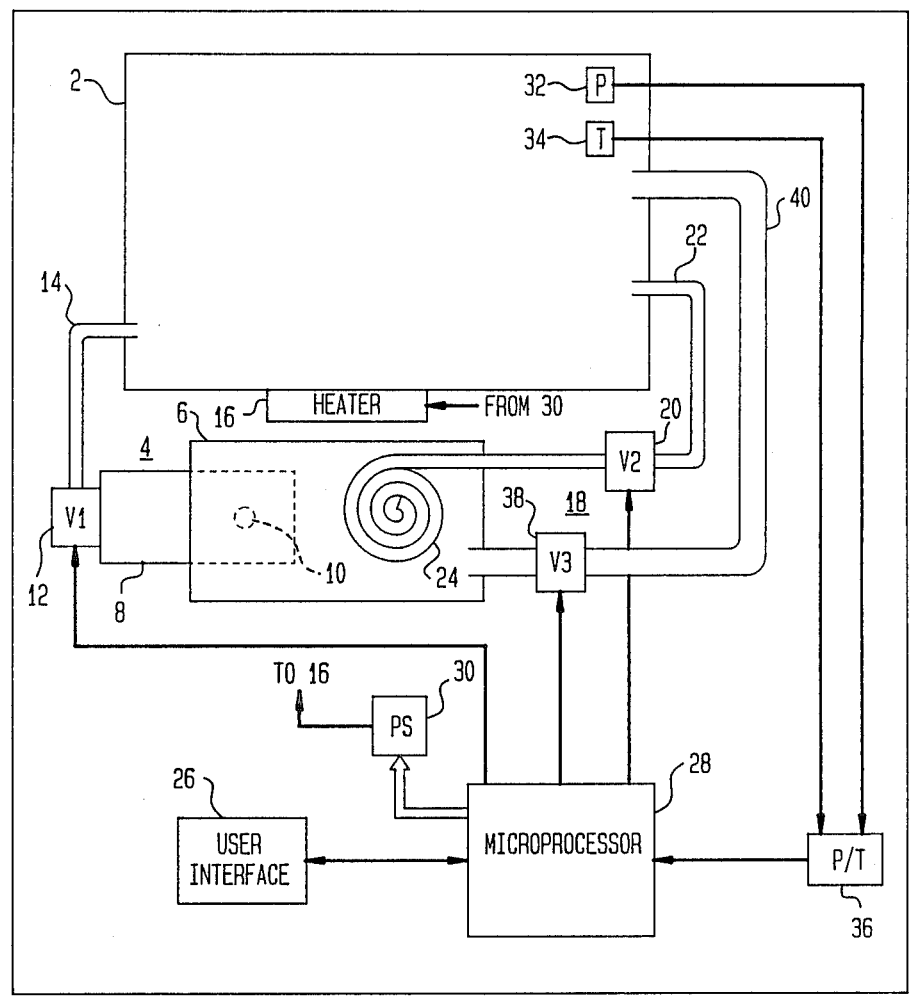

AUTOCLAVE VENT

BACKGROUND OF THE INVENTION

1. Field of the Invention

This invention relates to a vent arrangement for venting a gas, such as steam, from a pressurized chamber and in particular to a vent arrangement for venting steam from the chamber of an autoclave.

2. Description of the Prior Art

German Pat. No. 34 09 365 is typical of prior art vent arrangements for an autoclave of the type which includes a reservoir for supplying a liquid, such as water, into a sterilizing pressure chamber wherein the water is heated to generate a sterilizing steam. After the sterilizing cycle is over, it is necessary to exhaust the steam before the door of the chamber can be safely opened and the sterilized items removed. A solenoid controlled vent valve is normally provided for controlling the exhaust of steam from the chamber into a condensing coil located within the water reservoir. As the steam slowly vents through the condensing coil, it is changed into water and returned to the reservoir. Usually a heat cycle is provided after the steam is exhausted from the chamber, in order to dry the sterilized items.

It is desirable to vent the chamber of the steam as quickly as possible at the end of the sterilzing cycle, in order that the drying cycle can be started without delay. This reduces the total time needed for the sterilize/dry cycle.

Furthermore, sometimes the sterilized items are urgently needed and it would be desirable to be able to interrupt the autoclave cycling as soon as possible after the sterilization is complete, in order to give quick access to the sterilized items. The prior art arrangement requires a considerable period of time to completely vent all of the steam through the condensing coil, thereby prolonging the ending of the sterilize cycle.

SUMMARY OF THE INVENTION

In accordance with the principles of the present invention, the sterilizing pressure chamber of the autoclave is provided with two valve controlled vent paths. At the end of the sterilizing cycle a first vent path channels the steam from the chamber into a condensing coil having an end which opens into a liquid reservoir. When the pressure within the chamber drops to a predetermined level, a second vent path opens and provides a channel for the rapid escape of the remainder of the steam from the chamber.

BRIEF DESCRIPTION OF THE DRAWING

The sole FIGURE illustrates in block diagram form a top view of an autoclave including a vent arrangement constructed in accordence with the principles of the invention.

DETAILED DESCRIPTION OF THE PREFERRED EMBODIMENT

The mechanical portion of the autoclave of the FIGURE includes a sterilizing chamber 2 having a door (not shown) for allowing access by a user to items placed inside of chamber 2 to be sterilized. A dosing arrangement 4 includes a premeasured amount of liquid such as distilled water, into chamber 2. Dosing arrangement 4 includes a supply tank or reservoir 6 coupled to a dose tank 8 via a liquid flow path 10. The volume of dose tank 8 is substantially less than that of reservoir 6, and holds precisley that amount of water which is needed to produce the correct amount of steam inside chamber 2 for sterilization purposes. A solenoid oontrolled valve (V1)12 controls both the entrance of water into dose tank 8 and the flow of water from dose tank 8 into chamber 2 via an inlet line 14. Dosing arrangement 4 can be constructed in a variety of well known ways, e.g., as shown in the previously noted German Patent Publication No. 34 09 365 or as in German Patent Publication No. 32 25 982. Alternatively, dosing arrangment 4 can comprise the arrangement shown in U.S. patent application Ser. No. 45,968, filed concurrently herewith an having the same assignee as in the present application. A heater 16 attached about the outside circumference of chamber 2 is used to heat the water (via heating of the chamber) to make the sterilizing steam, and after the sterilize cycle is completed, to heat the air inside of chamber 2 in order to dry the sterilized items. A vent arrangement 18 is used to vent the steam from chamber 2 after the completion of the sterilization cycle. As is conventional in the prior art, vent arrangment 18 includes a solenoid operated valve (V2)20, for controlling the venting of steam, and any residual water, from chamber 2 into reservoir 6 via a flow path comprising an outlet line 22 and a condensing coil 24. Condensing coil 24 is located within reservoir 6 and slows the flow of the venting steam so as to allow it to be cooled by the water inside of reservoir 6 and return to a liquid phase.

The electronic portion of the autoclave includes a user interface 26 having control switches (not shown) for allowing a user to select an operating mode for the autoclave, e.g., a preset time/temperature/pressure cycle for sterilizing a selected type and quantity of items placed inside of chamber 2. A control microprocessor 28 is responsive to control signals from user interface 26 for operating valve 12 so as to control the flow of water into and out of dose tank 8, for operating valve 20 for controlling the venting of steam from chamber 2 and for controlling a power supply (PS) 30 which supplies power to heater 16. Power supply 30 is controlled by microprocessor 28 so as to cause heater 16 to generate the correct pressure and temperature of sterilizing steam during the sterilize cycle of the autoclave and heat during the dry cycle of the autoclave. The pressure and temperature conditions inside of chamber 2 are sensed by pressure (P) and temperature (T) sensors 32 and 34, respectively, and a pressure/temperature module (P/T) 36 coupled to sensors 30 and 32, provides pressure and temperature representative signals to microprocessor 28. Microprocessor 28 also provides control signals to display portions (not shown) of user interface 26, in order to provide the user with indications concerning the operation of the autoclave.

In accordance with the principals of the present invention, vent arrangement 18 includes a second vent path coupled in parallel with the first noted vent path. The second path has a flow rate which exceeds the flow rate of the first path and comprises a solenoid operated valve (V3) 38 for controlling the opening and closing of the flow path, i.e. exhaust line 40, coupled between chamber 2 and reservoir 6.

As previously noted, due to the operation of condensing coil 24, steam vents relatively slowly from chamber 2, thereby delaying the termination of the sterilize cycle and prolonging the time period before the sterilized items can be used. Due to the higher steam flow rate of exhaust line 40, when line 40 is opened, the steam pressure inside of chamber 2 rapidly decreases to zero, thereby allowing the user to safely open the door to chamber 2 relatively soon after the sterilize cycle is over, if desired, or allowing the dry cycle to quickly begin.

In operation, the user selects an operating mode for the autoclave via user interface 26. Microprocessor 28 controls valve 12 for emptying the water from dose tank 8 into chamber 2 and, via power supply 30, controls heater 16 for generating the correct pressure and temperature of sterilizing steam inside of chamber 2. As the chamber fills with steam, a conventional water/alcohol mixture operated air-bellows (not shown) coupled to chamber 2, vents the air displaced from chamber 2 into reservoir 6 via a flow path (not shown) connected to condensing coil 24. The increased temperature of the generating steam heats the water/alcohol mixture of the air-bellows, causing it to expand and close the air-bellows vent. After a predetermined pressure/temperature has been maintained for a predetermined amount of time, as determined by microprocessor 28, the sterilize cycle is over and microprocessor 28 causes valve 20 to open. During this time the steam pressure inside of chamber 2 slowly decreases from, e.g., 190 kPa, as the steam condenses into water via coil 24 and returns with any residual water from chamber 2, to reservoir 6. When the pressure as sensed by sensor 32 has dropped to a predetermined lower level, e.g., 20 kPa, microprocessor 28 causes valve 38 to also open, allowing the remaining steam to rapidly exhaust from chamber 2. Immediately thereafter, the door of chamber 2 may be opened and the sterilized items will be available for use or the dry cycle can begin. In the preferred embodiment valves 20 and 38 are not closed until after the next dose of water is supplied from dose tank 8 into chamber 2 for the next sterilize cycle.

One advantage to keeping valve 38 open until the start of the next sterilize cycle is to reduce an undersireable effect if the chamber door is opened while the chamber is hot, e.g. during sequential uses of the autoclave or interruptions during the heat cycle. When the door is opened, cool and relatively moist air enters the hot chamber and creates a partial pressurization which escapes while trying to again close the door. As long as valve 38 is open, a large flow rate path (exhaust line 40) is open between chamber 2 and the reservoir which prevents this build-up of partial pressure. An additional advantage is that the next dose of water can enter chamber 2 much more rapidly if valve 38 is open, since some steam is generated when the cool water is dumped into a hot chamber from the dose tank. In fact, in most prior art arrangements it was necessary to keep the chamber door open during the fill cycle to prevent the build-up of pressure which would inhibit the flow of water into the chamber during the fill cycle. With the present invention, the chamber door can be closed immediately after the items to be sterilized are placed inside the chamber, thereby reducing the operator involvement with the autoclave cycles and increasing the automatic operation of the autoclave. Furthermore, the dump valve remains open during the dry cycle. This feature advantageously allows easy exhaust of the moisture generated during the dry cycle, resulting in a more complete drying of the sterilized items or, alternatively, a shorter drying time. In summary, through various effects, the second vent path, i.e., exhaust line 40, is used to advantageously reduce the time required for the completion of several portions of the autoclave cycle, thereby reducing the total time required for the sterilizing operation and increasing the automation and effectiveness of the autoclave to the user.

Thus, there has been shown and described a novel apparatus for an autoclave vent arrangement. Many changes, modifications, variations, and other uses and applications of the subject invention will, however, become apparent to those skilled in the art after considering this specification and the accompanying drawing which discloses a preferred embodiment thereof. All such changes, modifications, variations and other uses and applications which do not depart from the spirit and scope of the invention are deemed to be covered by the invention which is limited only by the claims which follow.

What I claim is:

1. An autoclave, comprising:
    a supply tank for holding therein a supply of a liquid;
    a pressure chamber;
    dosing means coupled between said supply tank and said chamber for allowing the entry into said chamber of a predetermined amount of the liquid at the beginning of a sterilization cycle of said autoclave;
    a heater coupled to said pressure chamber for generating within said chamber a vapor phase of at-least a portion of the predetermined amount of liquid which is allowed to enter said chamber during said sterilization cycle;
    a first vent path means for venting the vapor phase of the liquid from said chamber into said supply tank at a first flow rate when open;
    a second vent path means for venting the vapor phase of the liquid from said chamber into said supply tank at a second flow rate which is greater than said first rate, when open;
    a microprocessor controller for controlling a plurality of time/temperature/pressure cycles for sterilizing items placed in said chamber;
    a pressure sensor arrangement for developing a signal representative of the pressure of the vapor phase of the liquid within said chamber; and
    wherein said microprocessor controller controls the opening of said first and second vent paths, said microprocessor controller being responsive to said pressure representative signal for controlling the opening of said second vent path at the end of said sterilize cycle.
2. The autoclave of claim 1, wherein:
    at the end of said sterilize cycle of said autoclave, said microprocessor controller first causes said first vent path to open, and when said pressure representative signal reaches a pressure level inside said chamber, causes said second vent path to open.
3. The autoclave of claim 1, wherein:
    said first vent path comprises a first vapor exhaust line having one end open to said chamber and another end coupled to an input of a first flow control valve and a condensing coil having one end open to said supply tank and another end coupled to an outlet of said first flow control valve.
4. The autoclave of claim 3 wherein:
    said second vent path comprises a second vapor exhaust line having one end open to said chamber, another end open to said supply tank and a second flow control valve coupled between said ends of said second vapor exhaust line.
5. The autoclave of claim 4, wherein:

said microprocessor controller is responsive to said pressure representative signal for controlling the opening of said second flow control valve.

6. The autoclave of claim 5, wherein:
at the end of said sterilize cycle of said autoclave, said microprocessor controller first causes said first flow control valve to open, and when said pressure representative signal reaches a predetermined level representative of a predetermined lower pressure level inside said chamber, causes said second flow control valve to open.

7. The autoclave of claim 6, wherein:
said microprocessor controller causes said second flow control valve to be open while said dosing means allows the entry into said chamber of the predetermined amount of the liquid at the beginning of said sterilize cycle.

8. The autoclave of claim 6, wherein:
said microprocessor controller causes said heater to heat said chamber after the end of said sterilize chamber, thereby causing a dry cycle of said autoclave; and
said microprocessor controller causes said second flow control valve to be open during said dry cycle.

9. The autoclave of claim 6, wherein:
said microprocessor controller causes said second valve to only be closed during said sterilize cycle.

* * * * *